United States Patent
Cembrowski (10) Patent No.: US 11,042,605 B2
(45) Date of Patent: Jun. 22, 2021

(54) METHOD AND APPARATUS FOR CALIBRATION AND TESTING OF SCIENTIFIC MEASUREMENT EQUIPMENT

(71) Applicant: CCQCC Corp., Edmonton (CA)

(72) Inventor: George S. Cembrowski, Edmonton (CA)

(73) Assignee: CCQCC Corp., Alberta (CA)

( * ) Notice: Subject to any disclaimer, the term of this patent is extended or adjusted under 35 U.S.C. 154(b) by 116 days.

(21) Appl. No.: 16/450,380

(22) Filed: Jun. 24, 2019

(65) Prior Publication Data

US 2020/0401653 A1 Dec. 24, 2020

Related U.S. Application Data

(63) Continuation-in-part of application No. 14/027,463, filed on Sep. 16, 2013, now Pat. No. 10,332,621, which is a continuation of application No. 12/841,055, filed on Jul. 21, 2010, now Pat. No. 8,538,727.

(60) Provisional application No. 61/227,348, filed on Jul. 21, 2009.

(51) Int. Cl.
*G06F 17/18* (2006.01)
*G01N 33/49* (2006.01)
*G01N 35/00* (2006.01)

(52) U.S. Cl.
CPC ............ *G06F 17/18* (2013.01); *G01N 33/49* (2013.01); *G01N 35/00693* (2013.01); *G01N 35/00871* (2013.01); *G01N 2035/00653* (2013.01)

(58) Field of Classification Search
CPC .. G06F 17/18; G01N 33/49; G01N 35/00693; G01N 35/00871; G01N 2035/00653
See application file for complete search history.

(56) References Cited

U.S. PATENT DOCUMENTS

| | | | |
|---|---|---|---|
| 4,202,033 A | 5/1980 | Strobel | |
| 4,627,014 A | 12/1986 | Lo et al. | |
| 4,858,154 A | 8/1989 | Anderson et al. | |
| 5,210,778 A | 5/1993 | Massart | |
| 5,360,613 A | 11/1994 | Nissen | |
| 5,366,896 A * | 11/1994 | Margrey | G16H 40/63 436/48 |
| 5,541,854 A | 7/1996 | Yundt | |
| 6,055,487 A * | 4/2000 | Margery | G01N 35/00871 702/84 |
| 6,157,041 A | 12/2000 | Thomas et al. | |
| 6,192,320 B1 * | 2/2001 | Margrey | G01N 35/00871 702/84 |

(Continued)

OTHER PUBLICATIONS

U.S. Appl. No. 12/841,055 , Response filed Oct. 15, 2012 to Non Final Office Action dated Apr. 13, 2012, 9 pgs.

(Continued)

*Primary Examiner* — Raymond L Nimox
(74) *Attorney, Agent, or Firm* — Schwegman Lundberg & Woessner, P.A.

(57) ABSTRACT

Discussed herein are systems, methods, and apparatuses for quality control monitoring of laboratory analyzers. A method can include receiving test results from laboratory analyzers, the test results corresponding to a same analyte, determining a standard deviation of differences (SDD) among pairs of the multiple test results, calibrating the laboratory analyzer based on the determined SDD.

16 Claims, 11 Drawing Sheets

(56) References Cited

U.S. PATENT DOCUMENTS

| | | | |
|---|---|---|---|
| 6,787,361 B1* | 9/2004 | Klee | G01N 33/50 436/43 |
| 8,538,727 B2 | 9/2013 | Cembrowski | |
| 10,332,621 B2 | 6/2019 | Cembrowski et al. | |
| 2003/0083901 A1 | 5/2003 | Bosch et al. | |
| 2003/0101012 A1* | 5/2003 | Parvin | G16H 10/40 702/84 |
| 2004/0078162 A1 | 4/2004 | Yundt-Pacheco | |
| 2007/0021856 A1* | 1/2007 | Popp | G05B 19/41875 700/110 |
| 2007/0198213 A1* | 8/2007 | Parvin | G16H 10/40 702/179 |
| 2007/0217949 A1* | 9/2007 | Mimura | G16H 10/40 422/63 |
| 2008/0186133 A1 | 8/2008 | Parkhurst et al. | |
| 2008/0312893 A1* | 12/2008 | Denton | G16H 10/40 703/11 |
| 2009/0119047 A1* | 5/2009 | Zelin | G01N 27/3274 702/82 |
| 2009/0131861 A1* | 5/2009 | Braig | A61B 5/150229 604/66 |
| 2009/0287356 A1 | 11/2009 | Dunne | |
| 2011/0022343 A1 | 1/2011 | Cembrowski | |
| 2011/0111439 A1 | 5/2011 | Hecker et al. | |
| 2014/0172311 A1 | 6/2014 | Cembrowski | |

OTHER PUBLICATIONS

U.S. Appl. No. 12/841,055, Non Final Office Action dated Apr. 13, 2012, 13 pgs.
U.S. Appl. No. 12/841,055, Notice of Allowance dated May 20, 2013, 12 pgs.
U.S. Appl. No. 12/841,055, Response filed Feb. 21, 2013 to Restriction Requirement dated Jan. 25, 2013, 79 pgs.
U.S. Appl. No. 12/841,055, Response filed May 6, 2013 to Restriction Requirement dated Jan. 25, 2013, 80 pgs.
U.S. Appl. No. 12/841,055, Restriction Requirement dated Jan. 25, 2013, 5 pgs.
U.S. Appl. No. 12/841,055, Supplemental Amendment filed May 9, 2013, 11 pgs.
U.S. Appl. No. 12/841,055, Supplemental Notice of Allowability dated Jul. 25, 2013, 6 pgs.
U.S. Appl. No. 14/027,463, Appeal Brief filed Feb. 21, 2017, 28 pgs.
U.S. Appl. No. 14/027,463, Appeal Decision mailed Aug. 28, 2018, 13 pgs.
U.S. Appl. No. 14/027,463, Examiner's Answer dated Jun. 12, 2017, 9 pgs.
U.S. Appl. No. 14/027,463, Final Office Action dated May 4, 2016, 13 pgs.
U.S. Appl. No. 14/027,463, Non Final Office Action dated Apr. 20, 2015, 12 pgs.
U.S. Appl. No. 14/027,463, Non Final Office Action dated Sep. 19, 2016, 15 pgs.
U.S. Appl. No. 14/027,463, Non Final Office Action dated Oct. 8, 2015, 12 pgs.
U.S. Appl. No. 14/027,463, Notice of Allowance dated Feb. 6, 2019, 7 pgs.
U.S. Appl. No. 14/027,463, Preliminary Amendment filed Nov. 5, 2013, 10 pgs.
U.S. Appl. No. 14/027,463, Reply Brief filed Aug. 14, 2017, 3 pgs.
U.S. Appl. No. 14/027,463, Response filed Jan. 8, 2016 to Non Final Office Action dated Oct. 8, 2016, 13 pgs.
U.S. Appl. No. 14/027,463, Response filed Jul. 14, 2015 to Non Final Office Action dated Apr. 20, 2015, 7 pgs.
U.S. Appl. No. 14/027,463, Response filed Aug. 26, 2016 to Final Office Action dated May 4, 2016, 14 pgs.
U.S. Appl. No. 14/027,463, Response filed Oct. 22, 2018 to Final Office Action dated Aug. 28, 2018, Amendment and Response to Final Office Action, 8 pgs.
Cembrowski, G. S., et al., "The use of serial patient blood gas, electrolyte and glucose results to derive biologic variation: a new tool to assess the acceptability of intensive care unit testing", Clin. Chem. Lab. Med., 48(10), (2010), 1447-1454.
Tran, D. V., et al., "Unique Approach to Derivation of Random Error in Laboratory Assays: Application to Glycohemoglobin Testing Demonstrates Poor Clinical Performance for Immunochemistry Assay", Diabetes Technology & Therapeutics, 5(6), (2003), 975-978.
Tran, D. V., et al., "Use of 2 years of patient data to estimate intra-laboratory total imprecision of HbA(1c) measured by multiple HPLC analyzers", Clinical Biochemistry, 41, (2008), 177-179.

* cited by examiner

METHOD AND APPARATUS FOR CALIBRATION AND TESTING OF SCIENTIFIC MEASUREMENT EQUIPMENT

PRIORITY APPLICATION(S)

This patent application is a continuation-in-part of and claims the benefit of priority to U.S. patent application Ser. No. 14/027,463, filed Sep. 16, 2013, which is a continuation of and claims the benefit of priority to U.S. patent application Ser. No. 12/841,055, filed Jul. 21, 2010, which claims the benefit of priority to U.S. Provisional Patent Application Ser. No. 61/227,348, filed Jul. 21, 2009, the benefit of priority of each of which is claimed hereby, and each of which are incorporated herein by reference in its entirety.

TECHNICAL FIELD

The inventive subject matter relates generally to scientific measurement equipment and devices, and more particularly to method and apparatus for testing, comparing and calibrating scientific measurement equipment and devices.

DETAILED DESCRIPTION

Clinical laboratory analyzers are used extensively in the medical and forensics profession and in research to perform tests on biological and other substances. The proper calibration and operation of these analyzers, and other laboratory equipment, is critical to producing accurate test results for patients and accurate measurements for researchers. As a result, proper use of such equipment requires regular recalibration. Such recalibration may be performed on a periodic basis based on the passage of time, or may be based on the number of uses of equipment between calibration, or based on a test of the equipment to determine its accuracy and recalibration only as necessary to maintain the desired accuracy level.

According to one example embodiment, there is described method, and apparatus, including programmed computers, to produce precision profiles for scientific measurement equipment in general, and in particular clinical laboratory analyzers. In this approach, either the analyzers' quality control data or serial patient data are numerically reduced to generate graphical precision profiles. Precision profiles for serial patient data show increased (im)precision vs time implying increased patient variation over increased time. Precision profiles for quality control data, according to one implementation, can demonstrate three different zones: 1) increased imprecision for quality control determinations that are close spaced (implies the discovery of an error condition and rapid reanalysis, 2) the usual imprecision and 3) a zone of increased imprecision which indicates either a need for a quality control analysis or re-calibration.

These precision profiles are used to summarize and compare the performance of the different analyzers that have produced these quality control or patient data. These precision profiles are also used to improve the quality control practices that are used with the analyzers.

To generate the quality control precision profile, on approach is to statistically summarize all of the quality control data that are generated for a particular test and quality control level (all of the qc data generated from the analysis of a one or more lots of quality control material of a single level over a period of several weeks to several years). To generate the patient data precision profile, one approach is to statistically reduce large volumes (at least 3 months) of patient data that are produced by hospital clinical laboratory analyzers, including point of care analytic systems.

Figure 1:
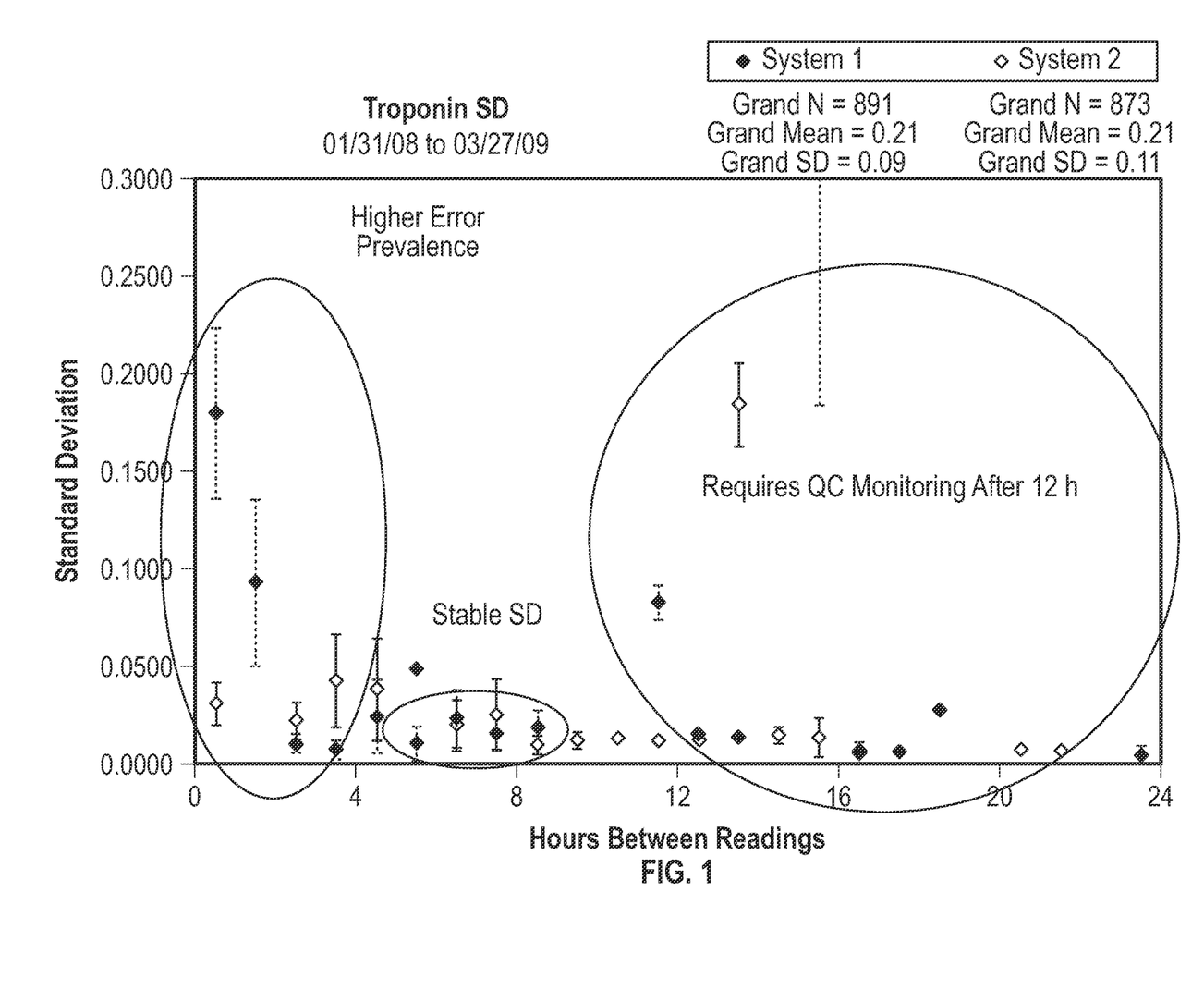
FIG. 1 shows a representative 24 hour precision profile graph for quality control data.
Figure 2:
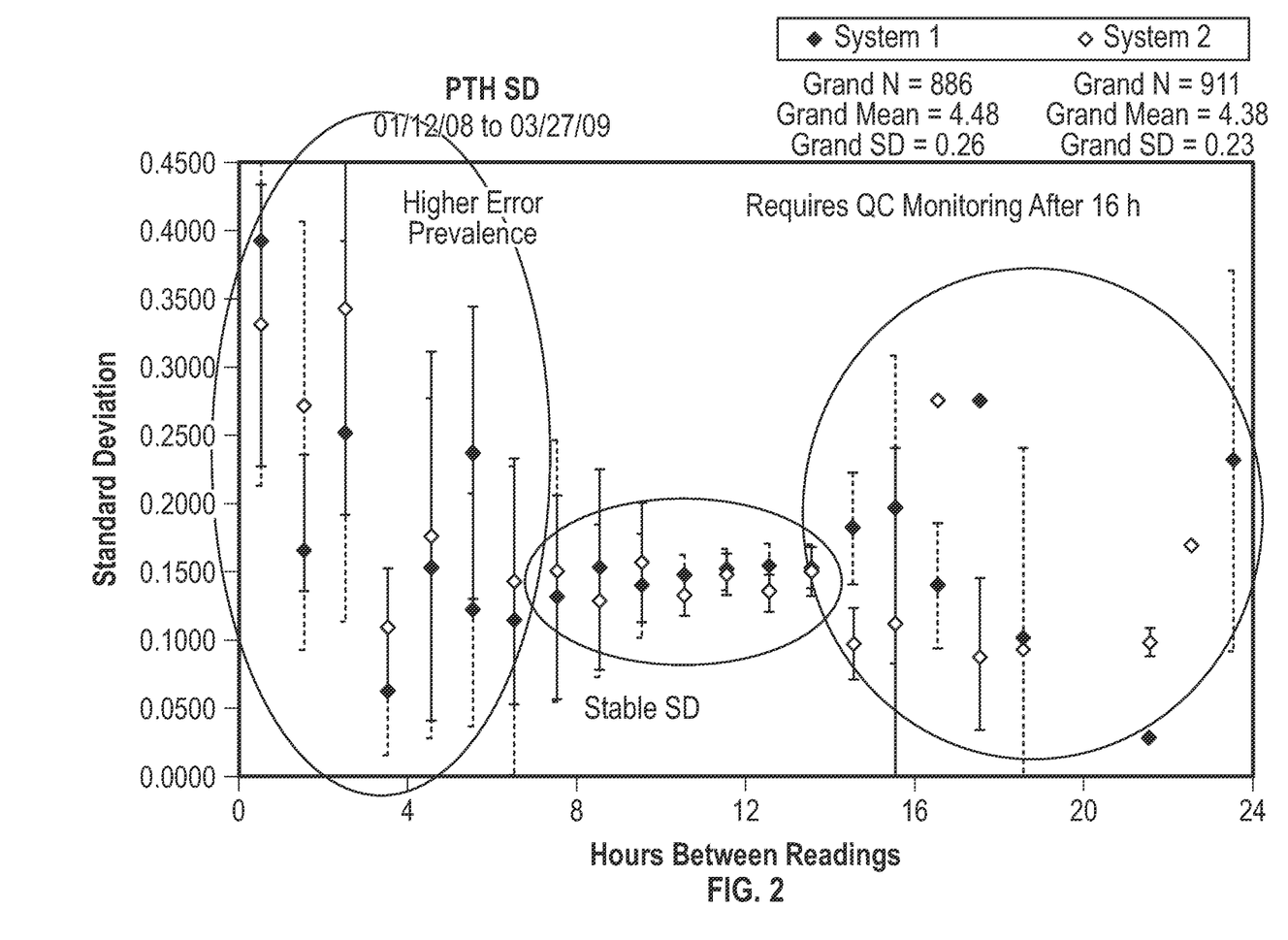
FIG. 2 shows a representative quality control precision profile graph.
Figure 3:
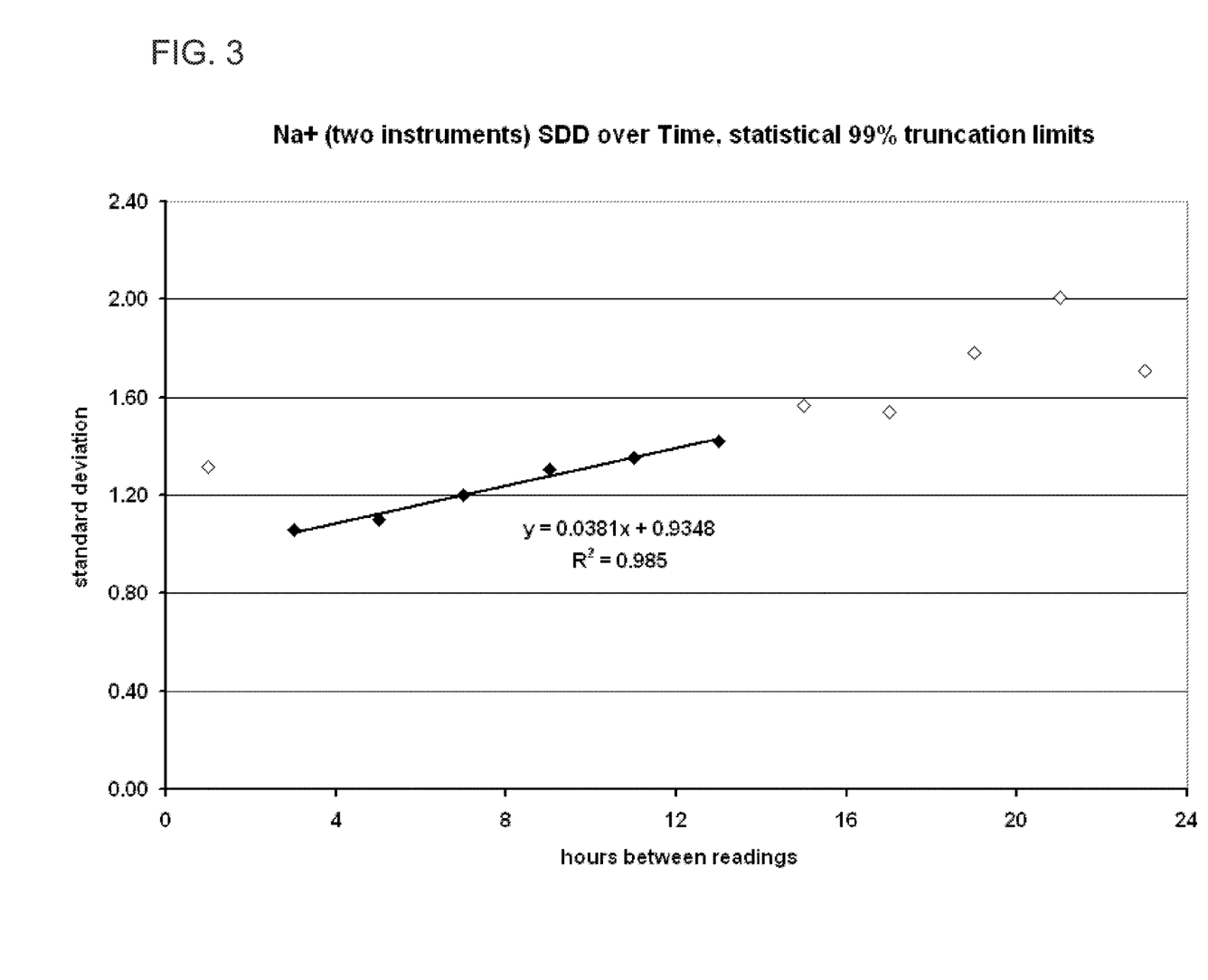
FIG. 3 shows a patient precision profile graph for sodium analyzed in an intensive care unit.

FIG. 1 is a graph showing a representative 24 hour precision profile for quality control data for the troponin (used to diagnose myocardial infarction) test and FIG. 2 is a graph showing a representative quality control precision profile for the PTH (parathyroid hormone) test. FIG. 3 is a graph showing a patient precision profile for sodium analyzed in an intensive care unit. These error vs. time profiles can be used to summarize and compare the analytic precision and indirectly the accuracy of different analytic technologies in the clinical laboratory.

According to one example embodiment, a precision profile may be used for quality control as follows:

- Determine the optimal quality control limits for the application of statistical quality control of the laboratory analyzer
- Demonstrate outlying quality control data
- Demonstrate the general times that analytic errors may be more prevalent
- Demonstrate when quality control specimens should be analyzed
- Compare analytic precision of similar systems in similar or different laboratory environments [referral laboratory, university hospital laboratory, near patient testing (point of care)].
- Use to educate laboratorian on appropriate quality control practices
- Use all the above to classify analyzers as in or out of compliance with quality control requirements and to determine how and when to calibrate the analyzers (measurement equipment in general)

According to another example embodiment, a precision profile may be used to provide a patient data precision profile as follows:

- Evaluate total analytic imprecision starting from blood drawing, to specimen processing to analysis and reporting
- Recommend how to use clusters of analyzers in the most appropriate manner (for example, if a laboratory has two systems, should it be using one system for a week or a month and not run the other or should there be alternation between the two systems, and what would be the most favorable period that each would be run before alternating to the other system)
- Help determine whether change of calibration frequency will improve quality of analytic results
- Compare analytic precision of different systems in different laboratory environments (referral laboratory, university hospital laboratory, near patient testing (point of care).

The process and compute programs for the data analysis which provides these profiles for both patient and quality control data is described in more detail in the attached paper: *The Use of Serial Patient Blood Gas Electrolyte and Glucose Results to Derive Biologic Variation*, the entirety of which is hereby incorporated herein by reference. This paper describes the analysis of patient data. Quality control data can be reduced in the same manner with one level of quality control representing one patient who is measured over the time of viability of the quality control product. Also attached and incorporated by reference are four studies: *Use of Patient Result-Derived Imprecisions to Assess the Analytic Quality of Electrolyte and Creatinine Measurements by Vitros and Beckman Methodologies, The Use of Serial Patient Blood Gas, Electrolyte and Glucose Results to Derive Biologic Variation: a New Tool to Gauge the Acceptability of ICU Testing, Use of Serial Patient Differences of HPLC HbA1c to Determine Long Term Instrument Performance*, and *Tandem Roche Hitachi 917, and Tandem Beckman LX-20 Operated in Two Tertiary Care Hospitals Exhibit Comparable Total Patient-Based Imprecisions*.

Figure 4:
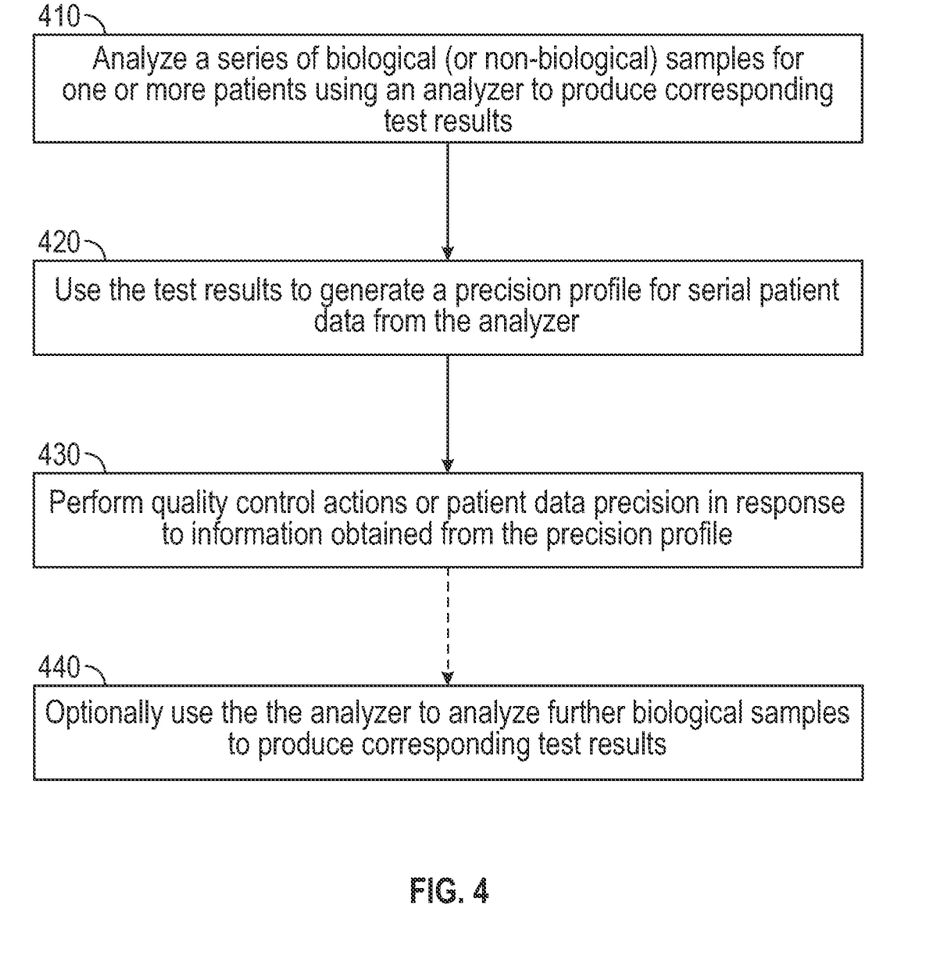
FIGS. 4 through 8 illustrate various methods and computer programs according to the inventive subject matter.

Thus, according to one example embodiment illustrated in FIG. 4, there is provided a method and corresponding computer program for generating and using a precision profile for a laboratory analyzer in particular, and scientific measurement equipment in general, including:

1. Analyze a series of biological (or non-biological) samples for one or more patients using an analyzer to produce corresponding test results (410).
2. Use the test results to generate a precision profile for serial patient data from the analyzer (420). The precision profile may comprise, for example, a graph that may demonstrate three different zones: 1) increased imprecision for quality control determinations that are close spaced (implies the discovery of an error condition and rapid reanalysis), such as shown in FIGS. 1-2 as the ellipse labeled "higher error prevalence"; 2) the usual imprecision, such as shown in FIGS. 1-2 as the ellipse labeled "standard SD"; and 3) a zone of increased imprecision which indicates either a need for a quality control analysis or re-calibration, such as shown in FIGS. 1-2 as the elliupse labeled "requires QC monitoring after 12 h" and "requires QC monitoring after 16 h," respectively.
3. Perform any of the actions set forth above for quality control or patient data precision in response to information obtained from the precision profile (430).
4. Optionally use the analyzer to analyze further biological samples to produce further corresponding test results (440).

Figure 5:
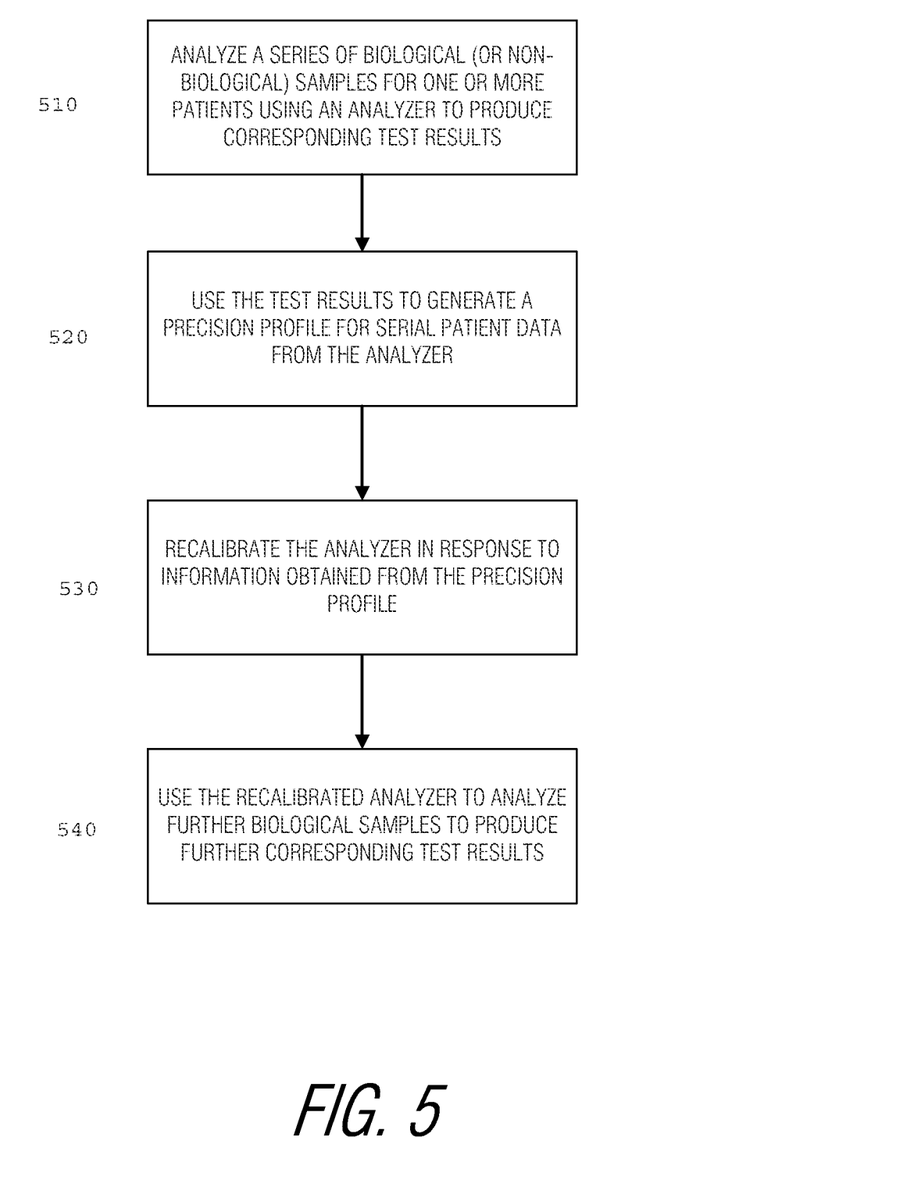

Thus, according to one example embodiment illustrated in FIG. 5, there is provided a method and corresponding computer program for calibrating a laboratory analyzer in particular, and scientific measurement equipment in general, including:

1. Analyze a series of biological (or non-biological) samples for one or more patients using an analyzer to produce corresponding test results (510).
2. Use the test results to generate a precision profile for serial patient data from the analyzer (520). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.
3. Re-calibrate the analyzer in response to information obtained from the precision profile (530).
4. Use the recalibrated analyzer to analyze further biological samples to produce further corresponding test results (540).

Figure 6:
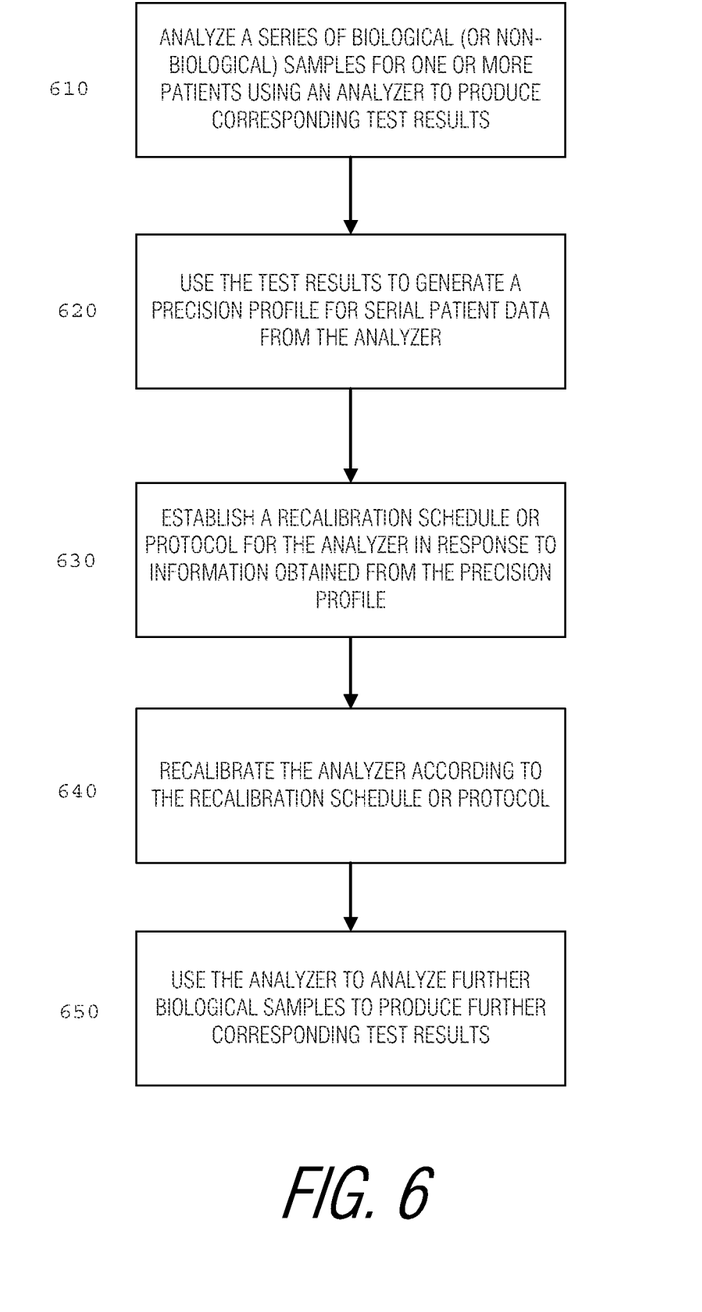

According to another example embodiment illustrated in FIG. 6, there is provided a method and corresponding computer program for establishing a calibration schedule or protocol for a laboratory analyzer in particular, and scientific measurement equipment in general, including:

1. Analyze a series of biological (or non-biological) samples for one or more patients using an analyzer to produce corresponding test results (610).
2. Use the test results to generate a precision profile for serial patient data from the analyzer (620). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.
3. Establishing a recalibration schedule or protocol for the analyzer in response to information obtained from the precision profile (630).
4. Recalibrating the analyzer according to the recalibration schedule or protocol (640).
5. Using the analyzer to analyze further biological samples to produce further corresponding test results (650).

Figure 7:
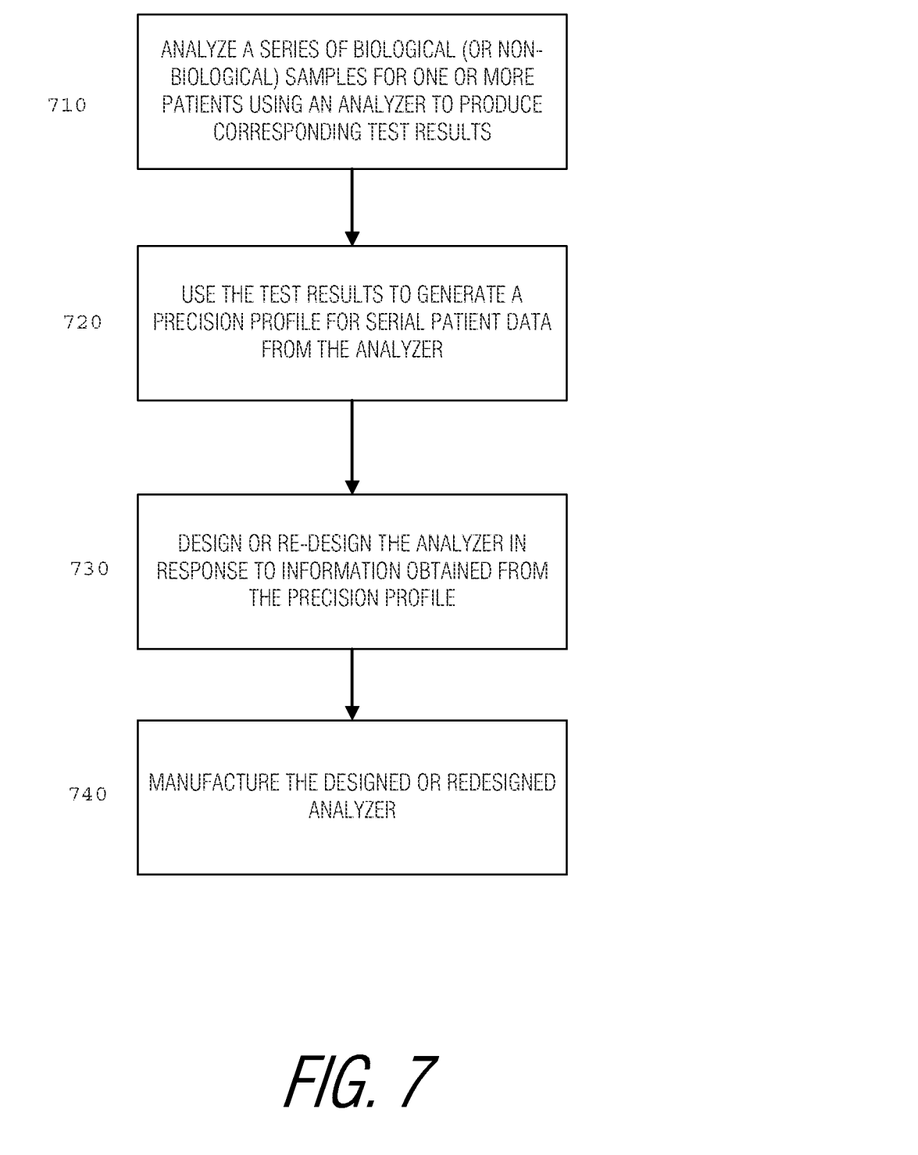

Thus, according to one example embodiment illustrated in FIG. 7, there is provided a method and corresponding computer program for designing or modifying the design of a laboratory analyzer in particular, and scientific measurement equipment in general, including:

1. Analyze a series of biological (or non-biological) samples for one or more patients using an analyzer to produce corresponding test results (710).
2. Use the test results to generate a precision profile for serial patient data from the analyzer (720). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.
3. Design or re-design the analyzer in response to information obtained from the precision profile (730).
4. Manufacture the designed or redesigned analyzer (740).

Figure 8:
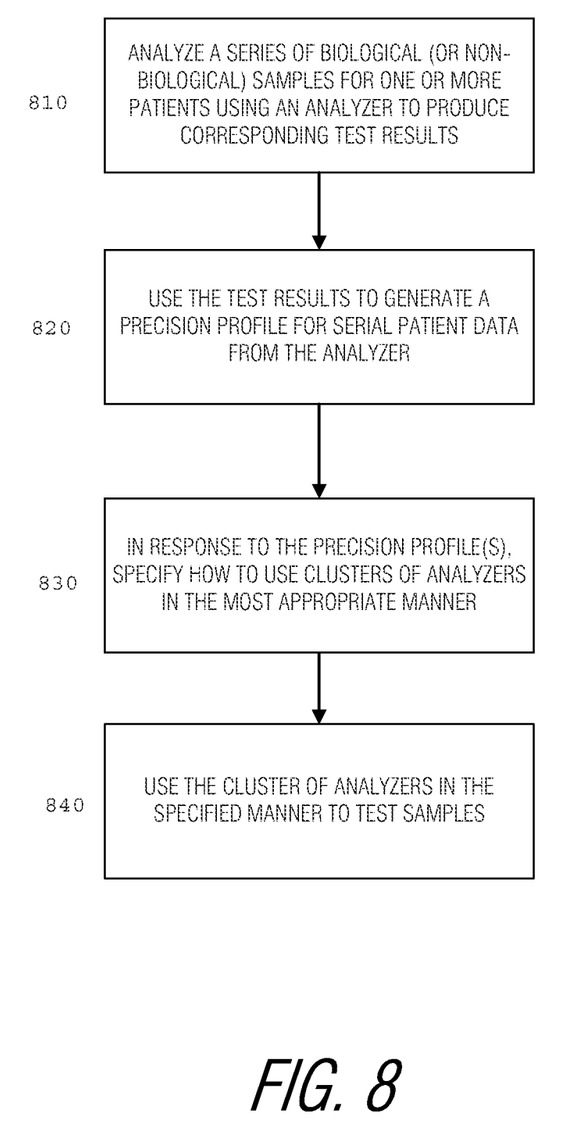

Thus, according to one example embodiment illustrated in FIG. 8, there is provided a method and corresponding computer program for developing a protocol for use of a cluster of laboratory analyzers in particular, and scientific measurement equipment in general, including:

1. Analyze a series of biological (or non-biological) samples for one or more patients using one or more analyzers to produce corresponding test results (810).
2. Use the test results to generate a precision profile for serial patient data from the analyzer(s) (820). The precision profile may comprise, for example, a graph that may demonstrate three different zones: 1)

increased imprecision for quality control determinations that are close spaced (implies the discovery of an error condition and rapid reanalysis), 2) the usual imprecision and 3) a zone of increased imprecision which indicates either a need for a quality control analysis or re-calibration.

3. In response to the precision profile or profiles, specifying how to use clusters of analyzers in the most appropriate manner (for example, if a laboratory has two systems, should it be using one system for a week or a month and not run the other or should there be alternation between the two systems, and what would be the most favorable period that each would be run before alternating to the other system) (830).

4. Using the cluster of analyzers in the specified manner to test samples (840).

Figure 9:
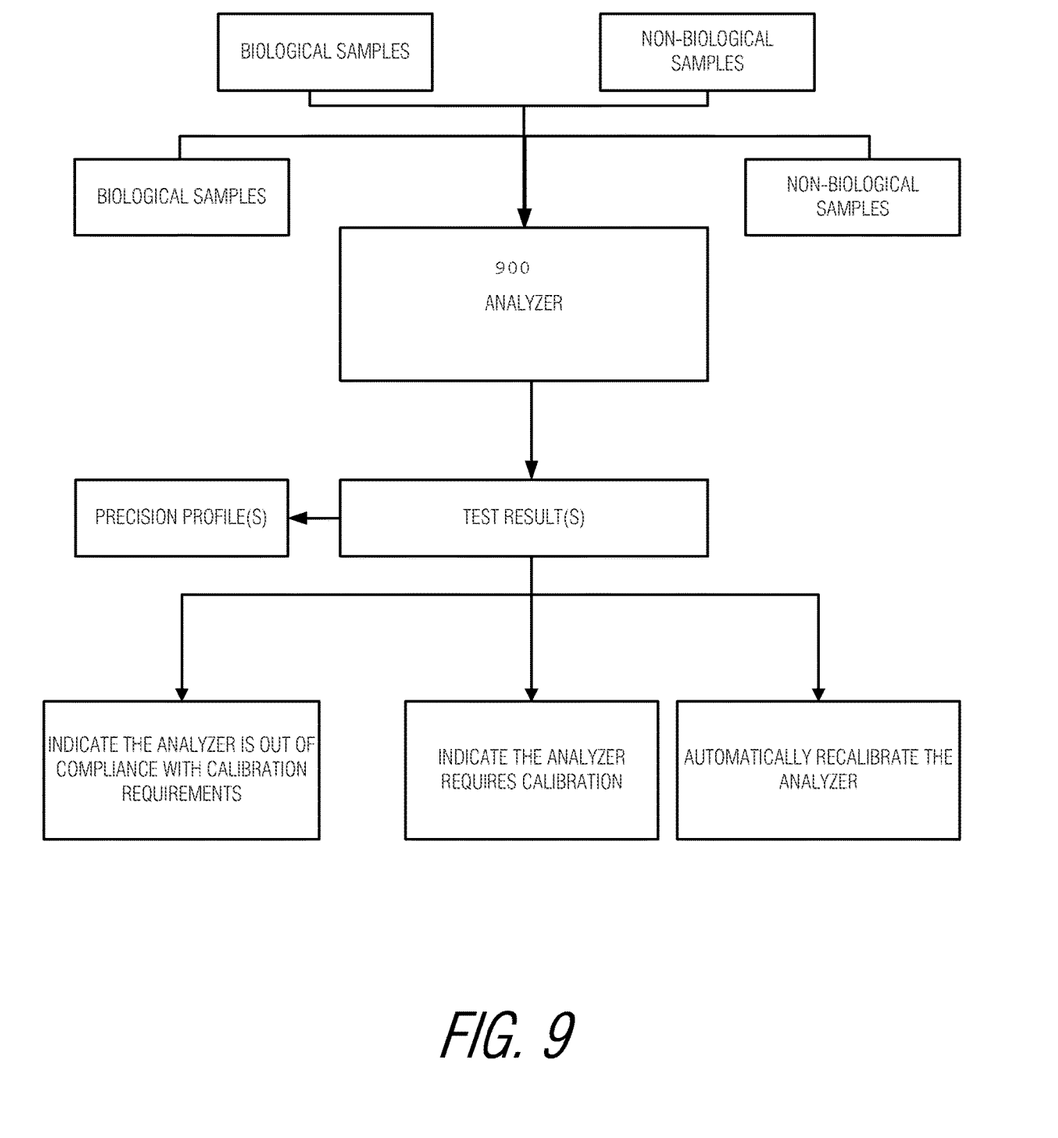
FIG. 9 illustrates a laboratory analyzer.
Figure 10:
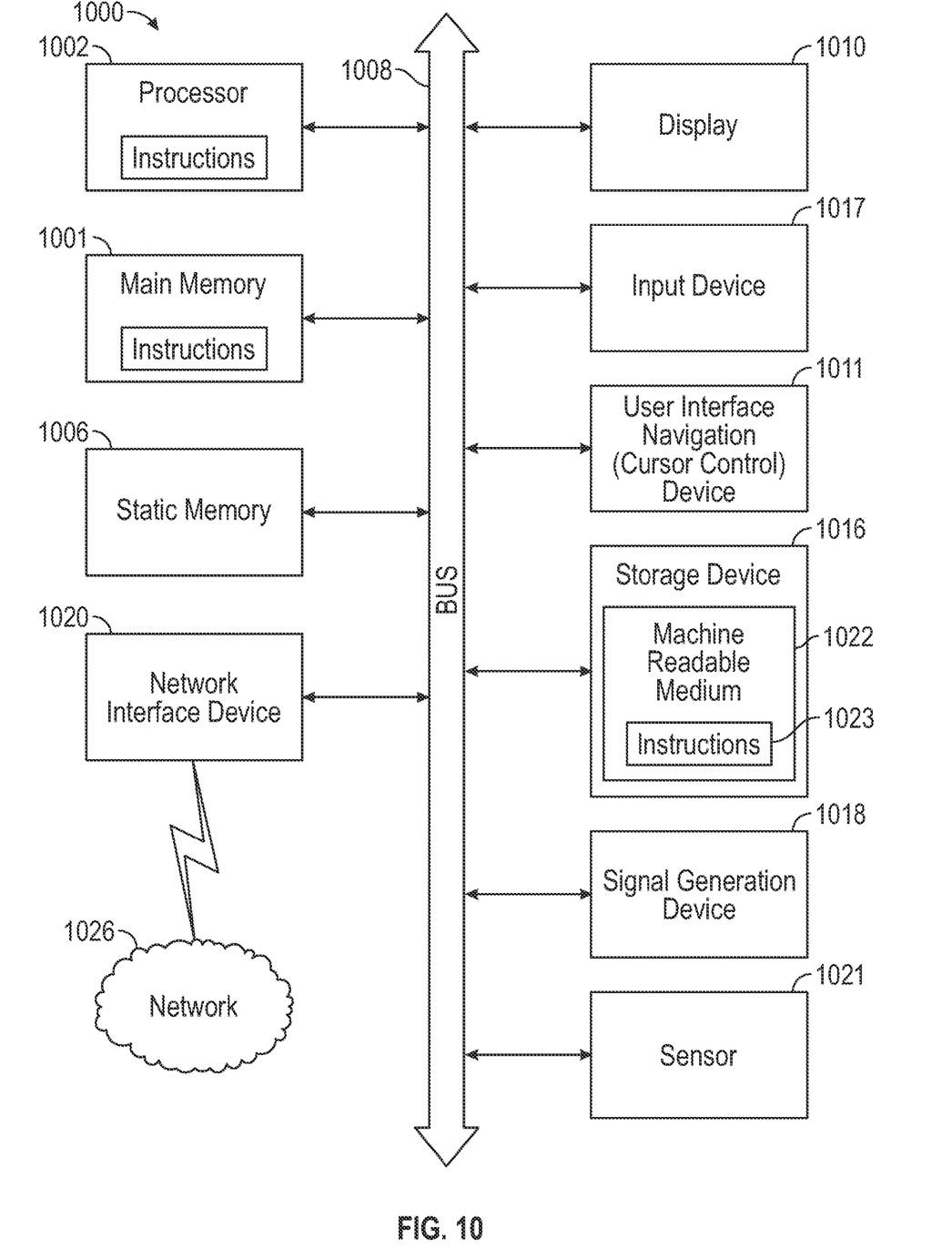
FIG. 10 illustrates a computer system.

According to one example embodiment, the computer programs that are used to implement all or any part of the processes described in FIGS. 4 through 8 may be executed on the computer system 1000 illustrated in FIG. 10, or executed on a computing system in analyzer 900 of FIG. 9.

Thus, according to one example embodiment illustrated in FIG. 9, there is provided a laboratory analyzer 900 that is capable of:

1. Analyzing a series of biological (or non-biological) samples for one or more patients using one or more analyzers to produce corresponding test results.
2. Analyzing the test results according to a computer process that is capable of producing all or a portion of a precision profile for serial patient data from the analyzer, and in response to the analysis of the test results automatically performing any one or more of the following:
   a. Indicating the analyzer is out of compliance with calibration requirements;
   b. Indicating the analyzer requires recalibration;
   c. Automatically recalibrating the analyzer.

Referring now to FIG. 10, there is illustrated a computer system 1000 that may be used to execute the computer programs described above with respect to FIG. 4 through 8, and can be used to generate the visual graphs illustrated in FIGS. 1 to 3. In addition, in one example embodiment, the analyzer 900 includes computer system 100 and one or more computer programs stored in its memories or storage unit to perform laboratory analytics, or execute the computer programs described herein to provide calibration.

More particularly, FIG. 10 is a block diagram of a machine in the form of a computing device within which a set of instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environments, or as a peer machine in peer-to-peer (or distributed) network environments. The machine may be a personal computer (PC), a tablet PC, a set-top box (STB), a Personal Digital Assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor 1002 (e.g., a central processing unit (CPU), a graphics processing unit (GPU) or both), a main memory 1001 and a static memory 1006, which communicate with each other via a bus 1508. The computer system 1500 may further include a display unit 1010, an alphanumeric input device 1017 (e.g., a keyboard), and a user interface (UI) navigation device 1011 (e.g., a mouse). In one embodiment, the display, input device and cursor control device are a touch screen display. The computer system 1000 may additionally include a storage device (e.g., drive unit 1016), a signal generation device 1018 (e.g., a speaker), a network interface device 1020, and one or more sensors 1021, such as a global positioning system sensor, compass, accelerometer, or other sensor.

The drive unit 1016 includes a machine-readable medium 1022 on which is stored one or more sets of instructions and data structures (e.g., software 1023) embodying or utilized by any one or more of the methodologies or functions described herein. The software 1023 may also reside, completely or at least partially, within the main memory 1001 and/or within the processor 1002 during execution thereof by the computer system 1000, the main memory 1001 and the processor 1002 also constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks.

The software 1023 may further be transmitted or received over a communications network 1026 using a transmission medium via the network interface device 1020 utilizing any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi® and WiMax® networks). The term "transmission medium" shall be taken to include any intangible medium that is capable of storing, encoding or carrying instructions for execution by the machine, and includes digital or analog communications signals or other intangible medium to facilitate communication of such software.

Recently, the Royal Alexandra Hospital, a large tertiary and quaternary level Edmonton, Alberta hospital replaced its 250 and 950 Vitros chemistry analyzers with two Beckman DxC 800 systems. During the conversion to the new analyzers, laboratory staff observed that the number of outliers increased relative to that previously. We have devised a data-mining statistic (within-patient imprecision regressed to zerotime between specimens) that summarizes the average short term analytic imprecision (sa) and minimized biologic patient variation (sb). This statistic can summarize the analytic imprecision over many reagent lots and calibrations.

We analyzed two 12 month periods of Vitros data and a single 10 month period of Beckman data. For chloride, CO2, creatinine, potassium and sodium, we tabulated the measurements of paired intra-patient samples drawn within 24 hours of each other. After outlier removal, we calculated the standard deviations of duplicates (SDD) of the intra-patient pairs grouped in two-hour intervals: 0-2 hours, 2-4 hours, 4-6 hours, ¼ 20-22 hours and 22-24 hours. The SDDs were then regressed against the time intervals of 2 to 14 hours; extrapolation to zero time (y-intercept) represents the average variation $(sa^2+sb^2)^{1/2}$. For each test, sa was calculated from the product of the short term within run experimental coefficient of variation (CV) and the control concentration. sb was calculated from sa and y0. CVb was determined by dividing sb by the average patient concentration. The uncertainity of CVb was derived from the standard error of the y-intercept; the relative error was obtained by dividing by the y-intercept.

sVitros was calculated using sb from Westgard.com. The increased imprecision due to using the Beckmans was derived from the square root of the differences of the squares of the SDD intercepts. The data mining tool, the within-patient imprecision regressed to zero-time between specimens, appears to be a powerful tool for evaluating imprecision.

Method stability and analytical imprecision are two of the most important criteria for instrument selection. We have devised a data-mining statistic (within-patient imprecision regressed to zero-time between specimens [WPI]) that summarizes the average short term analytic imprecision (sa) and minimizes biologic patient variation (sb). Unlike the short term analytic imprecision that is derived from quality control data, this statistic can summarize the analytic imprecision over many reagent lots and calibrations. Acute care hospitals and intensive care units provide adequate data to generate this imprecision statistic. This statistic can be used to compare the analytic performance of different analyzers operating in similar patient care environments.

This data-mining statistic is derived from the y intercept of the regression line of the standard deviations of intra-patient differences graphed against the time intervals between sampling. This statistic can summarize the analytic imprecision over many reagent lots and calibrations.

After outlier removal, we calculated the standard deviations of duplicates (SDD of the intra-patient pairs grouped in two-hour intervals: 0-2 hours, 2-4 hours, 4-6 hours. ¼ 20-22 hours and 22-24 hours. The WPI were obtained by regressing the SDDs against the time intervals of 2 to 14 hours; extrapolation to zero time (yintercept) represents the WPI. $(sa^2+sb^2)^{1/2}$.

Two groups of data were excluded from analysis: (1) Highly abnormal results which render the WPI calculation inaccurate. We generated frequency histograms of the patient data and in combination with the knowledge of reference intervals, we truncated significantly outlying data. (2) Results repeated within 2 hr. Reasons for serial testing within 2 hr include the investigation of a very morbid physiologic states, confirmation of very abnormal laboratory results and determining the response to an extreme therapy.

Quality controlling new assays using SDD.

We are witnessing relentless developments in diagnostic testing in the pursuit of longer life. Sadly, the new diagnostic tests are infrequently associated with the prevention or mitigation of common diseases such as obesity and smoking. Rather, the purpose of the new diagnostic tests is to diagnose less common but potentially catastrophic illnesses (e.g., sepsis, myocardial infarction, and rapidly progressive renal failure, among others). To assure timely treatment, the diagnosis of these disease states must be rapid and accurate with tolerably low false positive and false negative rates. The FDA recently approved an Early Sepsis Indicator from Beckman Coulter Diagnostics of Brea, Calif., United States. This test will be used to illustrate the importance of the SDD calculation in demonstrating acceptable analytical performance.

The Beckman Coulter DxH 900, a central laboratory hematology analyzer, has the capability to measure the Early Sepsis Indicator. It uses three different modalities to characterize monocyte white cells in their near-native states. Monocytes play a role in the dysregulated immune response to sepsis. Identifying morphological changes provides insight into possible sepsis earlier than other indicators.

It is the responsibility of the manufacturer to continuously demonstrate that their assays are robust and reliable. As such, the only approach to assure the accuracy and variation of a monocyte sizing measurement (and all sorts of other measurements) is with the analysis of serial patient measurements to provide the short-term and longer-term measures of patient data centrality and variation, via the SDD calculation. The inherent variation of the SDD calculation depends on the homeostatic mechanisms that tend to normalize the concentration of the measured analyte and the number of patient repeats. For analytes like electrolytes that are measured at the point of care, it has been found that a week of electrolyte data from an intensive care unit (ICU) can generate a stable SDD. For analytes that are more variably distributed, many more patient repeats are needed. A central laboratory analyzer is capable of producing many repeated tests compared to newer assays that will be provided at the point of care.

To implement the monitoring of a new test, such as monocyte sizing, and reliably diagnose high or low sepsis probabilities, it can be prudent to centralize the quality monitoring of the test. This is especially true during the initial test rollout. Depending on the test's stability and testing volume, weekly or biweekly estimates of either SDD or long term SDD can be compared for all participating centers. Intervention can occur in laboratories with statistically high SDD and might comprise remote instrument checks, reagent replacement, onsite manufacturer instrument support, laboratory analyzer calibration, or other adjustment to the laboratory analyzer. The SDD calculation is scalable and all of the differences can be incorporated in a single grand SDD calculation. Thus, if two or three laboratories are evaluators of a new reagent, all of the times and values of the serial measurements could be exported to an evaluator site where the SDD is calculated for each separate laboratory and/or the laboratories together.

Optimal use of the SDD calculations on point of care analyzers, especially with low numbers of test repeats (<50 patient repeats weekly).

As the SDD calculation is scalable, all patient repeats using the same lot number of reagents from roughly equivalent clinical care areas can be combined and used to produce a combined short-term or long-term SDD. Clinical care areas can be similar if they originate from the same country and thus exhibit similar style of clinical practice and similar socioeconomic standing. A test like troponin (a test for myocardial tissue death) that might be done on hundreds of analyzers in a country could be easily quality assured. All of the repeated data could be sent to central site and analyzed on a regular basis to provide SDD. As the SDD is a mixture of preanalytical, including patient variation and analytical variation (PAAN™), increases in PAAN could be related to its components. On a regular basis, each region's or sufficiently large site's SDD can be evaluated to discover situations that produce overly high SDD. Just like an isolated central hematology laboratory that is generating high SDDs, a region that is generating inordinately high SDDs can be investigated for origins of the high troponin variation, and a laboratory analyzer can be calibrated to account for the problem.

Such applications would be highly desirable in evaluations of new methods for regulatory approval. This approach is also useful after the assay is approved and used for clinical care. The distributed SDD determination can provide fundamental information for quality assurance, quality control and quality improvement.

Figure 11:
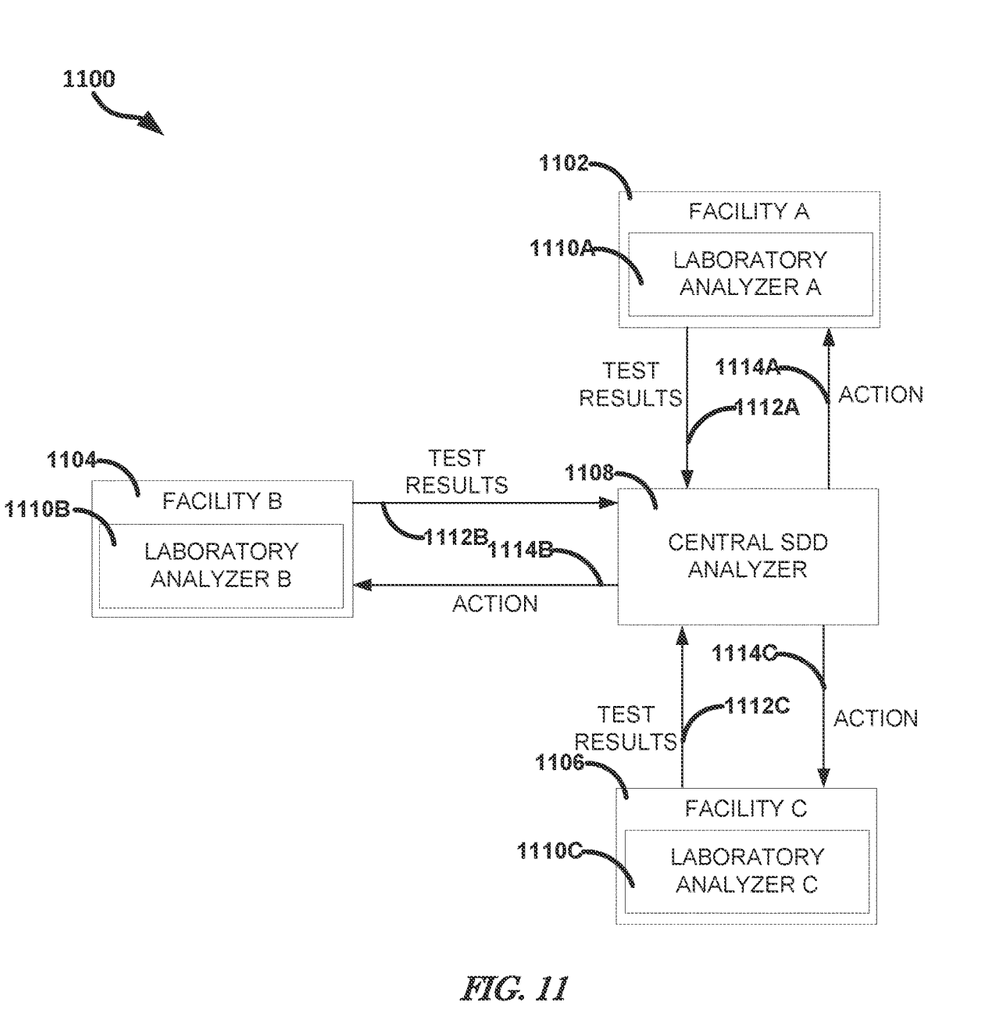
FIG. 11 illustrates a system for centralized determination of a distributed SDD.

FIG. 11 illustrates, by way of example, a diagram of an embodiment of a system 1100 for centralized SDD quality control via a distributed SDD. The system 1100 as illustrated includes laboratory analyzers 1110A, 1110B, 1110C in facilities 1102, 1104, 1106, respectively. The system 1100 further includes a central SDD analyzer 1108. Note that while each facility 1102, 1104, 1106 is illustrated as includes only a single laboratory analyzer 1110A-1110C, each facility can include more than one laboratory analyzer 1110A-1110C. Note that three facilities 1102, 1104, 1106 are illustrated, but there may be fewer or more facilities.

Test results 1112A, 1112B, 1112C from each respective laboratory analyzer 1110A, 1110B, 1110C can be provided to the central SDD analyzer 1108. The test results 1112A-1112C can include an analyte identification uniquely indicating the type of analyte analyzed by the laboratory analyzer 1110A-1110C to generate the test results 1112A-1112C (e.g., troponin, electrolyte, cell count, natriuretic peptide, calcium, alanine aminotransferase (ALT), albumin, alkaline phosphate, amikacin, ammonia, amphetamine, amylase, apolipoprotein A1 or B, aspartate aminotransferase (AST), vitamin B12, barbituates, benzodiazepine, bicarbonate, bile acids, bilirubin, BNP-32, buprenorphine, globulins, cannabis, carbamazepine, carboxyhaemoglobin, chloride, cholesterol, ciclosporin, citrate, cardiac marker CKMB, cocaine, cortisol, creatine kinase, creatinine, CRP, digoxin, D-dimeer, digoxin, eGFR, ethanol, ferritin, foetal fibronectin, folate, FOB, FIT, free T3 or T4, FSH, gamma glutamyl transferase, gentamicin, glucose, haematocrit, haemoglobin, HbA1c, hCG, HDL, heroin, HIV, homocysteine, IGFBP-1, INR, iron, ketamine, ketones, lactate, lactate dehydrogenase, lamotrigine, LDL, leucocytes, LH, lipase, lipoprotein, lithium, magnesium, methadone, mathaemoglobin, methamphetamine, methotrexate, myoglobin, nitrites, NT-pro BNP, Oestradiol, opiates, osmolality, oxalate, oxyhaemoglobin, pancreatic amylase, paracetamol, PBG, pCO2, pH, phenobarbital, phenytoin, phlGFBP-1, phosphate, plasma porphyrin, pO2, potassium, progesterone, prolactin, protein, renal calculi, salicylate, serum ACE, sirolimus, SHBG, sodium, specific gravity, tacrolimus, teicoplanin, testosterone, theophylline, TIBC, tobramycin, TUP, total T3 or T4, transferrin, triglyceride, troponin, TSH, urate, urea, urobilinogen, valproic acid, or vancomycin), a laboratory analyzer identification uniquely identifies the laboratory analyzer 1110A-1110C that generated the test results 1112A-1112C, a time/date at which the laboratory analyzer 1110A-1110C operated to generate the test results 1112A-1112C, a patient identification that uniquely (an anonymously) identifies the patient, a test facility identification that uniquely identifies the facility 1102, 1104, 1106, or an operator identification that uniquely identifies a lab technician that operated the laboratory analyzer 1110A-1110C.

The SDD analyzer 1108 can receive the test results 1112A-1112C and perform quality control calculations on the test results 1112A-1112C. The SDD analyzer 1108 can issue a communication indicating an action 1114A, 1114B, 1114C to be performed based on the analysis. For example, the SDD analyzer 1108 can determine an analytic variation based on the test results 1112A-1112C.

The SDD analyzer 1108 can first filter the test results 1112A-1112C to include only test results 1112A-1112C for a specified patient, facility 1102, 1104, 1106, laboratory analyzer 1110A-1110C, technician, date or time range, a combination thereof, or the like. The SDD analyzer 1108 can then determine analytic variation on a global scale, facility scale, laboratory analyzer scale, patient scale, time scale, or the like. These different SDD values can be interpreted by the SDD analyzer 1108. The SDD analyzer 1108 can issue a communication indicating the action 1114A-1114C (if any) is to be taken to compensate for an abnormal SDD. An abnormal SDD can be one that is more than a specified threshold (e.g., a half, one, or more standard deviations or variances away from an average).

The action 1114A-1114C can include results from multiple entities (e.g., facilities 1102, 1104, 1106, laboratory analyzers 1110A-1110C, technicians, patients, or the like). The results from multiple entities inform laboratory personnel of the quality of their analyte testing procedures, equipment, or personnel relative to others. The laboratory personnel can then take measures to improve quality of their procedures, calibrate or fix their equipment, re-train their personnel, or the like.

What is claimed is:

1. A method for calibration of a laboratory analyzer comprising:
   receiving test results from laboratory analyzers, the test results corresponding to a same analyte;
   determining a standard deviation of differences (SDD) among pairs of the multiple test results;
   calibrating the laboratory analyzer based on the determined SDD; and
   wherein the calibrated laboratory analyzer is used to generate further test results.

2. The method of claim 1 further comprising, before determining the SDD, filtering the test results based on a laboratory analyzer identification, and wherein determining the analytic variation includes determining the analytic variation for each laboratory analyzer of the multiple laboratory analyzers, and comparing the SDDs to identify a laboratory analyzer of the multiple laboratory analyzers to be calibrated.

3. The method of claim 1 further comprising, before determining the SDD, filtering the test results based on a facility identification uniquely indicating a facility of facilities that houses the laboratory analyzer, and wherein determining the analytic variation includes determining the analytic variation for each facility of the facilities, and comparing the SDDs to identify a facility of the multiple facilities that generates worse test results.

4. The method of claim 3, further comprising obtaining the test results by data-mining previous results provided by the laboratory analyzer.

5. The method of claim 1, further comprising grouping the test results by a time interval in which the sample results were provided, and wherein calculating the SDD variation includes calculating the SDD for each time interval.

6. The method of claim 1, further comprising removing out-lying test results before determining the SDD.

7. The method of claim 6, wherein removing out-lying test results includes removing out-lying test results as a function of a frequency histogram and removing test results from a repeated measurement made within a specific time period.

8. The method of claim 6, wherein removing out-lying test results includes removing test results from a repeated measurement made within two hours.

9. A system comprising:
multiple laboratory analyzers that perform measurements on one or more analytes to generate test results;
a memory storing the test results;
a processor communicatively coupled to the memory;
the memory storing instructions, which when executed by the processor, cause the processor to perform operations comprising:
receiving test results from laboratory analyzers;
determining a standard deviation of differences (SDD) among pairs of the multiple test results; and
causing the laboratory analyzer to be calibrated based on the determined SDD so the calibrated laboratory analyzer can be used to generate calibrated test results.

10. The system of claim 9, wherein the operations further comprise, before determining the SDD, filtering the test results based on a laboratory analyzer identification, and wherein determining the analytic variation includes determining the analytic variation for each laboratory analyzer of the multiple laboratory analyzers, and comparing the SDDs to identify a laboratory analyzer of the multiple laboratory analyzers to be calibrated.

11. The system of claim 9, wherein the operations further comprise, before determining the SDD, filtering the test results based on a facility identification uniquely indicating a facility of facilities that houses the laboratory analyzer, and wherein determining the analytic variation includes determining the analytic variation for each facility of the facilities, and comparing the SDDs to identify a facility of the multiple facilities that generates worse test results.

12. The system of claim 11, wherein the operations further comprise obtaining the test results by data-mining previous results provided by the laboratory analyzer.

13. The system of claim 9, wherein the operations further comprise grouping the test results by a time interval in which the sample results were provided, and wherein calculating the SDD variation includes calculating the SDD for each time interval.

14. The system of claim 9, wherein the operations further comprise removing out-lying test results before determining the SDD.

15. The system of claim 14, wherein the operations further comprise removing out-lying test results includes removing out-lying test results as a function of a frequency histogram and removing test results from a repeated measurement made within a specific time period.

16. The system of claim 14, wherein the operations further comprise removing out-lying test results includes removing test results from a repeated measurement made within two hours.

* * * * *